United States Patent [19] [11] 3,992,531
Prasad et al. [45] Nov. 16, 1976

[54] 2-SUBSTITUTED ADENOSINE-5'-CARBOXYLATES IN THE TREATMENT OF ANGINAL PAIN
[75] Inventors: Raj Nandan Prasad, Pierrefonds, Canada; Herman Hal Stein, Skokie, Ill.; Karin Rosemarie Tietje, Philipsburg, Canada
[73] Assignee: Abbott Laboratories, North Chicago, Ill.
[22] Filed: Sept. 13, 1974
[21] Appl. No.: 505,703

Related U.S. Application Data
[62] Division of Ser. No. 428,516, Dec. 26, 1973, Pat. No. 3,903,073.

[52] U.S. Cl. .................................. 424/180; 536/24
[51] Int. Cl.² ......................................... A61K 31/70
[58] Field of Search ................................... 424/180

[56] References Cited
UNITED STATES PATENTS
3,590,029 6/1971 Koch et al. .......................... 424/180

Primary Examiner—Lewis Gotts
Assistant Examiner—Cary Owens
Attorney, Agent, or Firm—Vincent A. Mallare; Robert L. Niblack

[57] ABSTRACT
2-Substituted adenosine-5'-carboxylates represented by the formula

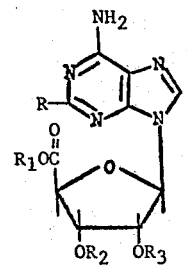

wherein R is amino, acetamido or hydroxy, $R_1$ is loweralkyl, haloloweralkyl, hydroxyloweralkyl, lowercycloalkyl, loweralkenyl, loweralkynyl, loweralkyl($C_3$–$C_6$)cycloalkyl or alkoxyalkyl and $R_2$ and $R_3$ each are hydrogen or acyl, or $R_2$ and $R_3$ taken together form an isopropylidene or benzylidene moiety; and the pharmaceutically acceptable acid addition salts thereof. The compounds wherein $R_2$ and $R_3$ are hydrogen or acyl are useful in treating cardiovascular disorders and are particularly useful as anti-anginal agents. Compounds wherein $R_2$ and $R_3$ when taken together form an isopropylidene or benzylidene moiety are intermediates useful in making the final products.

2 Claims, No Drawings

2-SUBSTITUTED ADENOSINE-5'-CARBOXYLATES IN THE TREATMENT OF ANGINAL PAIN

This is a division of application Ser. No. 428,516 filed Dec. 26, 1973, and now U.S. Pat. No. 3,903,073 issued Sep. 2, 1975.

DETAILED DESCRIPTION OF THE INVENTION

The present invention relates to 2-substituted-adenosine derivatives, to therapeutic compositions containing such derivatives as the active ingredients, and to methods of preparing and using the compounds as well as intermediates useful in the preparation of such compounds.

The compounds of this invention are represented by the formula

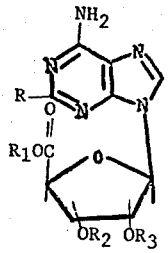

wherein R is amino, acetamido or hydroxy, $R_1$ is loweralkyl haloloweralkyl, hydroxyloweralkyl, lowercycloalkyl, loweralkenyl, loweralkynyl, loweralkyl($C_3$–$C_6$)cycloalkyl or alkoxyalkyl and $R_2$ and $R_3$ each are hydrogen or acyl, or $R_2$ and $R_3$ taken together form an isopropylidene or benzylidene moiety; and the pharmaceutically acceptable acid addition salts thereof.

The term "loweralkyl" refers to both straight and branched chain $C_1$–$C_6$ alkyls including methyl, ethyl, n-propyl, iso-propyl, n-butyl, sec-butyl, tert-butyl, iso-butyl, n-pentyl, iso-pentyl, neo-pentyl, hexyl and the like.

"Loweralkenyl" refers to the $C_2$–$C_5$ alkyl groups as defined above, from which a hydrogen atom has been removed from each of two adjacent carbon atoms to produce ethylenic unsaturation; e.g., vinyl, allyl, methallyl, 1-pentenyl and the like.

"Loweralkynyl" refers to the $C_2$–$C_5$ alkyl groups as defined above, from which two hydrogen atoms have been removed from each of two adjacent carbon atoms to produce acetylenic unsaturation; e.g., ethynyl, propargyl, 2-butynyl, 1-pentynyl and the like.

"Halo" includes chloro, fluoro, bromo or iodo.

"Loweralkyl($C_3$–$C_6$)cycloalkyl" includes cyclopropylmethyl, cyclobutylethyl and the like.

The term "alkoxyloweralkyl" refers to alkoxyalkyl groups having no more than 6 carbon atoms, such as methoxymethyl, ethoxyethyl, methoxyethyl, propoxypropyl, propoxyethyl and the like.

The term "pharmaceutically acceptable acid addition salts" refers to non-toxic salts prepared by reacting the ester with an appropriate organic or inorganic acid, or by utilizing an acid addition salt of the appropriate intermediate. Representative salts include the hydrochloride, hydrobromide, sulfate, bisulfate, acetate, valerate, oleate, laurate, borate, benzoate, lactate, phosphate, tosylate, citrate, maleate, succinate, tartrate, napsylate and the like.

The term "acyl" refers to acetyl, propionyl, butyryl and the like.

Compounds of this invention wherein $R_2$ and $R_3$ are hydrogen or acyl are useful as anti-anginal agents at dosages of from 0.1 to 10 mg./kg. of body weight daily. While oral dosages are preferred, the compounds exhibit both oral and parenteral activity. While the compounds can be administered in a single dose, it is preferred to administer them in divided dosages, i.e., 3 to 4 times daily.

The anti-anginal activity of the compound of this invention was first established using the method of Schoepke et. al., Pharmacologist 8; 204 (1966).

Compounds of this invention wherein $R_2$ and $R_3$ are acyl or when taken together form an isopropylidene or benzylidene moiety are useful as intermediates for preparing compounds wherein $R_2$ and $R_3$ are hydrogen.

Generally speaking, compounds of this invention are prepared from 2-acetamido-adenosine-5'-carboxylic acid or from the corresponding 2',3'-isopropylidene derivatives. 2-acetamido-adenosine-5'-carboxylic acid is obtained by reacting 2,6-diaminopurine sulfate with sodium hydroxide to obtain 2,6-diaminopurine which is then reacted with acetic anhydride to yield 2,6-diacetamidopurine, which in turn is converted to a mercuri chloride complex. The mercuri chloride complex of 2,6-diacetamidopurine is then reacted with triacetyl D-ribofuranosyl chloride to obtain 2,6diacetamido-9-(triacetyl-$\beta$-D-ribofuranosyl) purine, which is then converted to the corresponding 2-acetamido adenosine by treatment with methanol in the presence of ammonia. Preparation of 2-acetamido adenosine from 2,6-diaminopurine sulfate has been described by J. Davoll & B. A. Lowy [J.A.C.S., 73, 1650 (1951)]. The corresponding isopropylidene compound is obtained by reacting 2-acetamido adenosine with acetone. Potassium permanganate oxidation affords the corresponding 5'-carboxylic acid.

From 2',3'-isopropylidene-2-acetamido-adenosine-5'-carboxylic acid, one can prepare the protected 5'-carboxylic acid derivatives and then cleave the isopropylidene moiety or the cleaving of the isopropylidene moiety can be effected first and then the 5'-carboxylates conveniently obtained by reacting the 5'-carboxylic acid with the appropriate alcohol ($R_1OH$) in the presence of thionyl chloride. The corresponding 2-amino and 2-hydroxy derivatives can be conveniently obtained from the 2-acetamido derivatives.

The following reaction schemes further illustrate the reaction sequences employed in the preparation of the compounds of this invention.

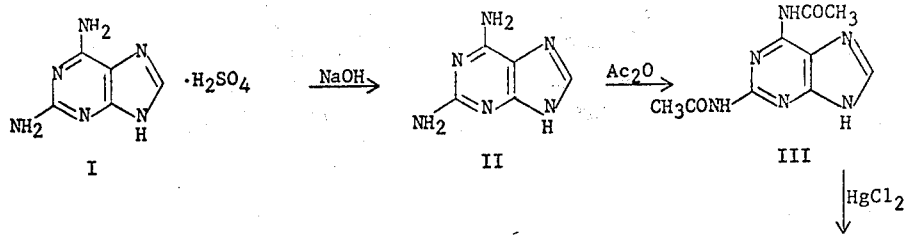

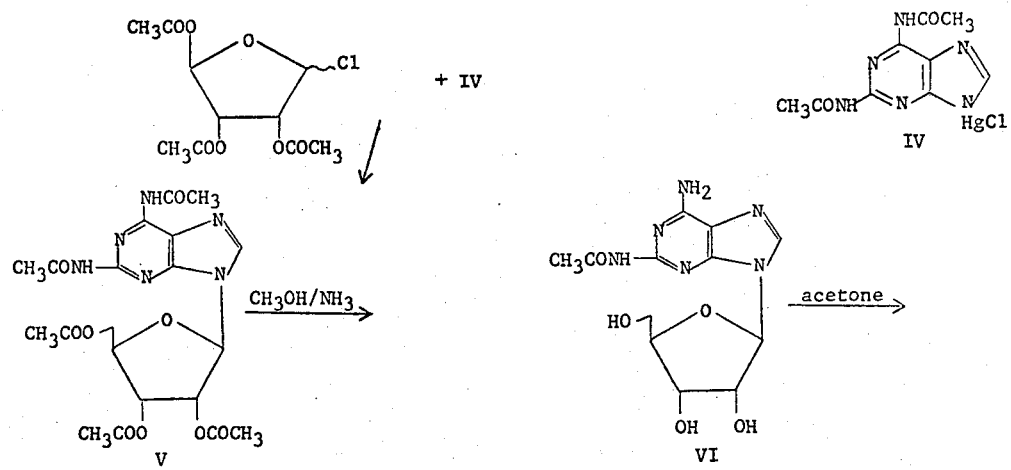
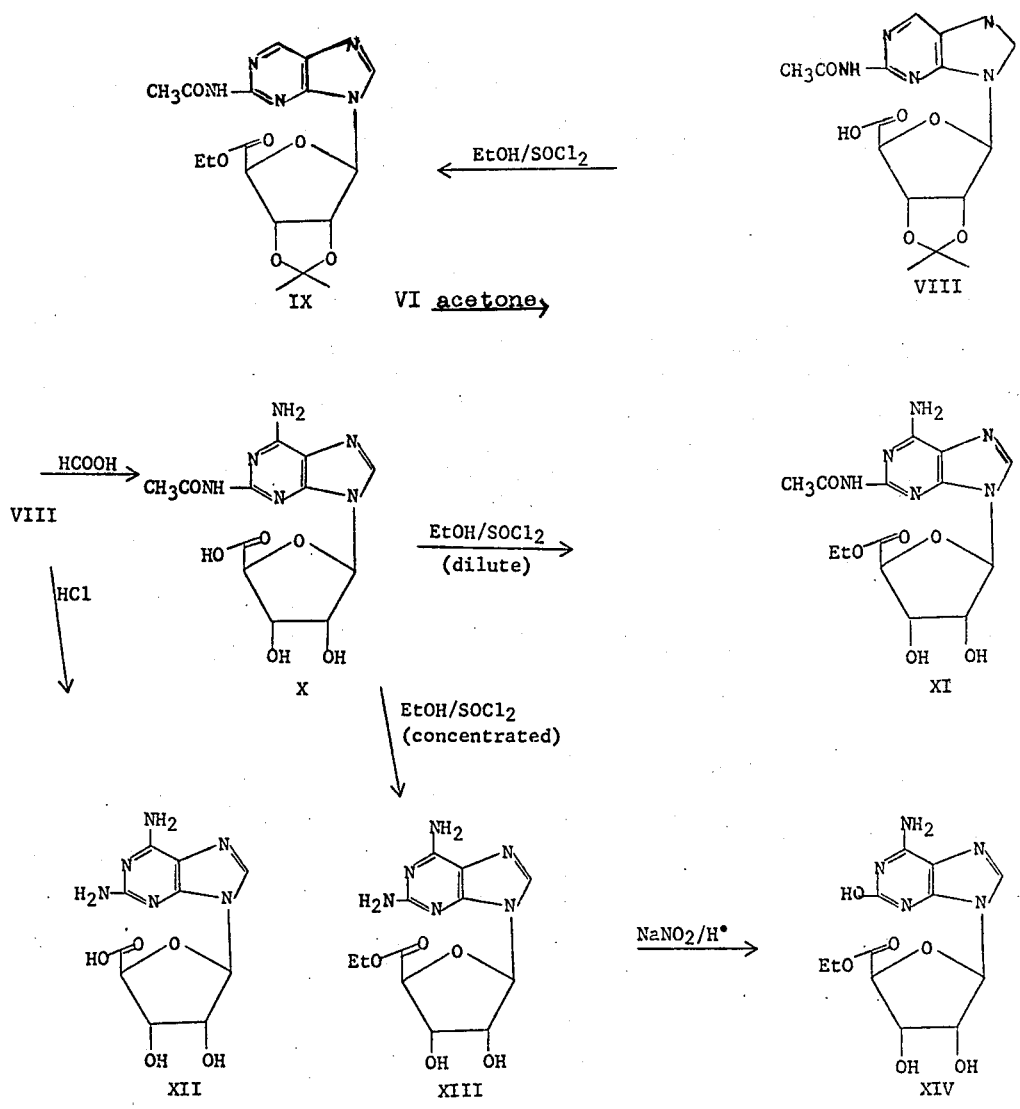

The following examples further illustrate the present invention.

EXAMPLE 1

2,6-Diaminopurine (II)

A solution of 2,6-diaminopurine sulfate (100 g., 0.5 mole) in boiling aqueous NaOH solution (20 g., NaOH 2.5 1 water) was stirred with charcoal and filtered hot. The filtrate, on cooling, deposited cream colored solid, which was filtered, washed successively with cold water, acetone, ether and dried to give 55.5 g. (74%) of 2,6-diaminopurine (m.p. 270°).

EXAMPLE 2

2,6Diacetamidopurine (III)

A suspension of dried 2,6diaminopurine (55.5 g., 0.372 mole) in acetic anhydride (900 ml.) was stirred and refluxed for 3 hours. The reaction mixture was left overnight at room temperature, cooled, filtered and washed successively with ether, ethanol and ether. The crystalline 2,6diacetamidopurine(81.5 g., 95%) was dried at 60° for 15 hours in vacuo.

EXAMPLE 3

Chloromercuri Derivative of 2,6-Diacetamidopurine (IV)

A solution of NaOH (14.0 g., 0.35 mole) in 50% ethanol was added to 2,6-diacetamidopurine (81.5 g., 0.35 mole) dissolved in boiling 50% ethanol (2.5 1); followed immediately by a solution of mercuric chloride (95 g., 0.35 mole) in absolute ethanol. The amorphous precipitate, which separated, was left overnight at room temperature, cooled, filtered and washed with 50% ethanol, ether and dried in vacuo at room temperature over $P_2O_5$.

Yield, 145.0 g. (88.5%) of the chloromercuri derivative of 2,6diacetaminopurine.

EXAMPLE 4

2,6-Diacetamido-9-(Triacetyl-$\beta$-D-Ribofuranosyl)Purine (V)

(Note: Glass wares used in these experiments were dried at 100° C., all the starting materials and solvents were bone-dry and used under anhydrous conditions.)

a. Triacetyl D-Ribofuranosyl Chloride

A stirred suspension of 1,2,3,5-tetra acetyl-$\beta$-D-ribofuranoside (16.0 g., 0.05 mole) in dry ether (360 ml.) was saturated at 0°C. with dry HCl gas (dried by bubbling through concentrated $H_2SO_4$). When a clear solution was obtained, the reaction mixture was left at room temperature for 1 hour, and then evaporated under reduced pressure. The residue was diluted with $CCl_4$ and the solution was evaporated again under reduced pressure. This process of dilution with $CCl_4$ and evaporation under reduced pressure was repeated a few times until all the acetic acid was removed. The residual oil was finally taken up in xylene and immediately used as described in b.

b. The dried chloromercuri derivative (24 g., 0.05 mole) of 2,6-diacetamidopurine was refluxed in xylene using a Dean-Stark water separator. Freshly prepared triacetyl-D ribofuranosyl chloride in xylene was added to the hot chloromercuri derivative and the mixture was refluxed, in an oil bath, with vigorous stirring. After 4½ hours the reaction mixture was allowed to stand overnight at room temperature and then filtered. The precipitate was extracted (several times) with warm $CHCl_3$. The $CHCl_3$ extract was washed successively with 30% aqueous KI (thrice), water (thrice) dried, charcoaled and filtered. The filtrate was evaporated in vacuo, and the residue on trituration with ether gave 14.3 g. (58%; m.p. 87°–92°) of 2,6-diacetamido-9-triacetyl-$\beta$-D-ribofuranosyl purine.

EXAMPLE 5

2-Acetamido-6-Amino-9-$\beta$D-Ribofuranosylpurine or 2-Acetamido Adenosine (VI)

2,6-Diacetamido-9-triacetyl-$\beta$-D-ribofuranosylpurine (16.0 g., 0.0325 mole) was dissolved in hot methanol (100 ml.) and then cooled to 5° C. A cold methanolic solution (400 ml.) obtained by saturating methanol with $NH_3$ at 0°C., was added to the above purine riboside and left at 5° C. for 24 hours. The clear solution was evaporated and the residual solid was recrystallized from boiling water (norite) to give 7.0 g. (67%) of 2-acetamido adenosine after drying at 60° ($P_2O_5$).

EXAMPLE 6

2-Acetamido-6-Amino-2',3'-O-Isopropylidene-9-$\beta$-D-Ribofuranosylpurine or 2-Acetamido-2',3'-O-Isopropylidene Adenosine (VII)

A suspension of VI (7.3 g., 0.0225 mole) in dry acetone (1.5 1) was mixed with p-toluene sulfonic acid monohydrate (43 g., 0.225 mole) and stirred. A clear solution which resulted immediately gave heavy precipitate in 5 minutes. After stirring for 15 hours at room temperature, solid $NaHCO_3$ (70 g.) was added and stirring was continued for another 24 hours. The solids were separated by filtration and filtrate was evaporated to dryness. The residue on trituration with ether gave 6.7 g. (82%) of the product, VII, melting at 197°–203°; $R_f$ 0.56 ($CHCl_3$:MeOH: 9: 1).

EXAMPLE 7

2-Acetamido-2', 3'-O-Isopropylidene Adenosine-5'-Carboxylic Acid (VIII)

Powdered VII (2.5 g., 0.00687 mole) was suspended in warm water (400 ml.) and cooled to room temperature. Most of the solid (VII) was is solution. To this stirred solution, aqueous KOH (1.15 g., 0.0206 mole in 30 ml. $H_2O$) was added, followed by a slow addition (1.5 hour) of aqueous $KMnO_4$ was destroyed by the dropwise addition of 20% $H_2O_2$ (at 5°–10°) until there was no more pink color. The precipitated manganese dioxide was removed by filtration through celite. The clear filtrate was brought to PH 7 to 7.5 and then evaporated to near dryness below 40° C. under reduced pressure. The pH was then adjusted to 5–6 by dilute HCl and the solution was evaporated to dryness under reduced pressure. The residue was repeatedly extracted with boiling absolute ethanol. The ethanol extract on evaporation gave 2.0 g. (77%) of VIII having an indefinite melting point (160° . . . 176° . . . 197° dec.).

Confirmation of VIII was obtained by converting it into its ethyl ester (IX) as described below. A mixture of VIII (0.4 g., 0.00105 mole) is absolute ethanol (60 ml.) and $SOCl_2$ (0.5 ml.) at room temperature, was stirred for 15 hours and then evaporated (under reduced pressure) to dryness below 30° C. The residue was dissolved in aqueous $NaHCO_3$ solution at 10° C. and the basic solution was extracted a few times, first with CHCl₃ and then with ethyl acetate. The organic extracts were combined, dried and evaporated to dryness to give 0.64 g., (15%) (recrystallized from abslute ethanol) of the ethyl ester (IX) melting at 221°–22° having the characteristic ir peak at 1740 cms⁻¹.

Analysis calcd. for $C_{17}H_{22}N_6O_6$: C,50.24; H, 5.46; N, 20.68. Found: C,50.31; H, 5.59; N, 20.88.

Nmr confirmed the structure of IX.

EXAMPLE 8

2-Acetamido Adenosine-5′-Carboxylic Acid (X)

A solution of VIII (2.0 g., 0.0053 mole) in 50% formic acid (80 ml.) was kept at 70° for 75 minutes and then evaporated to dryness under reduced pressure. The residue was mixed with a little water and evaporated again. This process was repeated a few times to give 0.8 g. (45%) of the desired product (X) melting at 295° dec. Infra red spectra (KBr) showed the characteristic 1715 cms⁻¹ peak. The compound was insoluble in every solvent except aqueous base.

EXAMPLE 9

2-Acetamido Adenosine-5′-(Ethyl) Carboxylate (XI)

Thionyl chloride (7 drops) was added to a suspension of dry X (0.2 g., 0.00059 mole) in absolute ethanol (50 ml.) at 10° C. The mixture was stirred at 10°C. The mixture was stirred at 10° C. for 1 hour and at room temperature for 15 hours. The clear solution was concentrated in vacuo, at 25° C. and the residual liquid was diluted with ether. The hygroscopic hydrochloride salt precipitated was taken up in ice-water basified with aqueous NaHCO₃ at 10° C. and the precipitate was filtered (0.1 g., 48%). Purification by solution in cold dilute HCl and its precipitation by dilute NH₄OH gave the pure product (XI) melting at 251°–52° dec. Nmr confirmed its structure. TLC showed the product to be homogeneous ($R_f$ 0.76) in n-butanol/CH₃COOH/H₂O (5:2:3) system.

Analysis Calcd. for $C_{14}H_{18}N_6O_6$: C, 45.90; H, 4.95; N, 22.94. Found: C, 45.59; H, 4.96; N, 23.06.

EXAMPLE 10

2-Amino Adenosine-5′-Carboxylic Acid (XII)

A mixture of 2-acetamido-2′,3′-O-isopropylidene adenosine-5′-carboxylic acid (VIII; 1.0 g., 0.0026 mole) in 1N HCl was kept at 60°–65° for 30 minutes. The reaction mixture was then cooled, basified with 50% NaOH and acidified with acetic acid. The precipitate was filtered, washed successively with water and ethanol to give 0.2 g. (23%; m.p. 228°) of 2-amino adenosine-5′-carboxylic acid (XII); UV max (MeOH) 223, 248 and 278 nm.

EXAMPLE 11

2-Amino Adenosine-5′-(Ethyl) Carboxylate (XIII)

Thionyl chloride (2.5 ml.) was added dropwise to a suspension of 2-acetamido-adenosine-5′-carboxylic acid (X, 2.5 g., 0.0074 mole) in absolute ethanol (120 ml.) at 0°C. After stirring for an hour at 0°C., the reaction mixture was stirred overnight at room temperature. The mixture was cooled, diluted with ether and filtered to give 1.9 g. of the (dry) hydrochloride salt. The salt was dissolved in water and basified with NaHCO₃ solution. The precipitate was filtered, washed successively with water, ethanol, ether and dried in vacuo over P₂O₅ to give 1.2 g. (44%) of 2-amino-adenosine-5′-(ethyl) carboxylate as a monohydrate melting at 215°–216° dec. Nmr and mass spectra confirmed its structure; UV max (MeOH) 221, 258 and 278 nm.

Analysis Calcd. for $C_{12}H_{16}N_6O_5\cdot H_2O$: C, 42.11; H, 5.30; N, 24.55. Found: C, 42.07; H, 4.78; N, 24.55.

The mother liquor (after the removal of 1.2 g. of XIII) was evaporated to dryness at 30° C. under reduced pressure. The residue was washed with ether and then stirred with aqueous NaHCO₃ solution. The insoluble residue was filtered (0.147 g. m.p. 247°–49° dec.) and identified as 2-acetamido adenosine-5′-(ethyl) carboxylate [XI, UV max MeOH) 225, 271 nm].

EXAMPLE 12

2-Hydroxyadenosine-5′(ethyl)carboxylate or Isoguanosine-5′-(Ethyl) Carboxylate (XIV)

Glacial acetic acid (1.2 ml.) was added to a suspension of 2-amino adenosine-5′-(ethyl) carboxylate (XIII, 0.5 g., 0.00137 mole) in water (15 ml.) at 0°–5° C. A solution of NaNO₂ (1.13 g., 0.0164 mole) in water (5 ml.) was added to the above suspension and stirred. First at 0°–5° C. for ½ hour and then at room temperature for 15 hours. At the end of this period, the mixture was cooled and the product (XIV, 0.22 g., m.p 268–69° dec.) was filtered and washed with a little cold water. The compound (XIV) analyzed as a monohydrate. Nmr and mass spectra confirmed the presence of one amino and three hydroxy groups in the molecule. It (XIV) is assumed to have the isoguanosine structure based on the results of nitrous acid reaction of 2-amino adenosine [J. Davol. J. Amer. Chem. Soc. 73, 3174 (1951)]. The UV spectrum showed λ max/MeOH 215, 249, 297 nm.

Analysis Calcd. for $C_{12}H_{15}N_5O_6\cdot H_2O$: C, 41.98; H, 4.99; N, 20.40. Found: C, 41.85; H, 4.84; N, 20.38.

We claim:

1. A method of treating anginal pain in a patient in need of such treatment which consists essentially of administering to said patient a dosage of from 0.1 to 10 mg./kg. of body weight daily of a compound of the formula

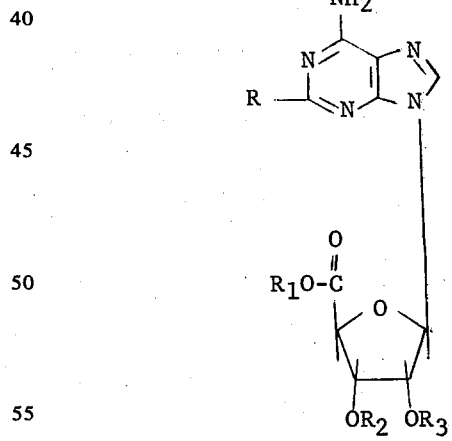

wherein R is amino, acetamido or hydroxy, R₁ is loweralkyl, haloloweralkyl, hydroxyloweralkyl, lowercycloalkyl, loweralkenyl, loweralkynyl, loweralkyl(C₃–C₆.)cycloalkyl, alkoxyalkyl or hydrogen and R₂ and R₃ each are hydrogen or acyl; and the pharmaceutically acceptable acid addition salts thereof.

2. A pharmaceutical composition in unit dosage form which consists essentially of 6.0 to 700.0 mg. of a compound of claim 1 and a pharmaceutically acceptable carrier.

* * * * *